US011545255B2

(12) United States Patent
Sun et al.

(10) Patent No.: US 11,545,255 B2
(45) Date of Patent: Jan. 3, 2023

(54) SYSTEMS AND METHODS FOR CLASSIFYING AN ANOMALY MEDICAL IMAGE USING VARIATIONAL AUTOENCODER

(71) Applicant: SHANGHAI UNITED IMAGING INTELLIGENCE CO., LTD., Shanghai (CN)

(72) Inventors: Shanhui Sun, Lexington, MA (US); Zhang Chen, Brookline, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 388 days.

(21) Appl. No.: 16/722,429

(22) Filed: Dec. 20, 2019

(65) Prior Publication Data
US 2021/0193298 A1    Jun. 24, 2021

(51) Int. Cl.
*G16H 30/40* (2018.01)
*G06N 20/00* (2019.01)
(Continued)

(52) U.S. Cl.
CPC .......... *G16H 30/40* (2018.01); *G06K 9/6277* (2013.01); *G06N 7/005* (2013.01); *G06N 20/00* (2019.01); *G06V 10/757* (2022.01)

(58) Field of Classification Search
CPC ........ G16H 30/40; G06N 20/00; G06N 7/005; G06V 10/757; G06K 9/6277;
(Continued)

(56) References Cited

U.S. PATENT DOCUMENTS

2009/0016579 A1*  1/2009  White ................... G16H 10/20
                                                          382/128
2016/0239969 A1*  8/2016  Davatzikos .......... G06K 9/6247
(Continued)

FOREIGN PATENT DOCUMENTS

WO    WO-2019197644 A1 * 10/2019 ............. A61B 5/055

OTHER PUBLICATIONS

Matsubara et al. "Deep Generative Model using Unregularized Score for Anomaly Detection with Heterogenous Complexity", Journal of Latex Class File, vol. 14, No. 8, Aug. 2015 (Year: 2015).*
(Continued)

*Primary Examiner* — Vu Le
*Assistant Examiner* — Julius Chai
(74) *Attorney, Agent, or Firm* — Faegre Drinker Biddle & Reath LLP

(57) ABSTRACT

Methods and systems for classifying an image. For example, a method includes: inputting a medical image into a recognition model, the recognition model configured to: generate one or more attribute distributions that are substantially Gaussian when inputted with a normal image; and generate one or more attribute distributions that are substantially non-Gaussian when inputted with an abnormal image; generating, by the recognition model, one or more attribute distributions corresponding to medical image; generating a marginal likelihood corresponding to the likelihood of a sample image substantially matching the medical image, the sample image generated by sampling, by a generative model, the one or more attribute distributions; and generating a classification by at least: if the marginal likelihood is greater than or equal to a predetermined likelihood threshold, determining the image to be normal; and if the marginal likelihood is less than the predetermined likelihood threshold, determining the image to be abnormal.

18 Claims, 8 Drawing Sheets

(51) Int. Cl.
*G06K 9/62* (2022.01)
*G06N 7/00* (2006.01)
*G06V 10/75* (2022.01)

(58) Field of Classification Search
CPC . G06K 9/00503; G06T 7/0012; G06T 7/0014; G06T 7/002; G06T 7/136; G06T 7/143
See application file for complete search history.

(56) References Cited

U.S. PATENT DOCUMENTS

2020/0020098 A1* 1/2020 Odry .................... G06N 3/0454
2021/0343012 A1* 11/2021 Xiao .................... G06T 7/0012

OTHER PUBLICATIONS

Zong et al., "Deep Autoencoding Gaussian Mixture Model for Unsupervised Anomaly Detection", International Conference on Learning Representation, 2018 (Year: 2018).*

* cited by examiner

SYSTEMS AND METHODS FOR CLASSIFYING AN ANOMALY MEDICAL IMAGE USING VARIATIONAL AUTOENCODER

1. BACKGROUND OF THE INVENTION

Certain embodiments of the present invention are directed to object recognition. More particularly, some embodiments of the invention provide methods and systems for classifying an anomaly medical image using variational autoencoder. Merely by way of example, some embodiments of the invention are configured to classify a medical scan image. But it would be recognized that the invention has a much broader range of applicability.

Many medical examinations involve scanning patients using tools such as MR, CT, and PET scanners to guide diagnosis or treatment planning. One common challenge is identifying poor scan images which do not comply with a quality standard, such as ones that do not provide clear or accurate information. In one example, a poor scan image may result from a patient not able to stay still, such as by not holding breath, during a scan. Poor scan images are typically unusable for clinical decision-making and therefore are generally discarded and rescanned. Rescanning a patient, especially for imaging techniques that requires long process time, such as PET image reconstruction that involves attenuation and scatter correction, leads to great inefficiency. Images that are not up to standard, which are sometimes referred to as anomaly images, regardless of the scanning technique, are generally required to be manually identified and discarded by an imaging technician, such as prior to sending images to a radiologist. Generally, a technician would browse a set of images and identify anomaly images, which not only is a slow process, but also prone to human error. Therefore, systems and methods for identifying anomaly medical images with improved efficiency and accuracy are desirable.

2. BRIEF SUMMARY OF THE INVENTION

Certain embodiments of the present invention are directed to object recognition. More particularly, some embodiments of the invention provide methods and systems for classifying an anomaly medical image using variational autoencoder. Merely by way of example, some embodiments of the invention are configured to classify a medical scan image. But it would be recognized that the invention has a much broader range of applicability.

In various embodiments, a computer-implemented method for classifying a medical image includes: inputting a medical image into a recognition model, the recognition model configured to: generate one or more attribute distributions that are substantially Gaussian when inputted with a normal image, and generate one or more attribute distributions that are substantially non-Gaussian when inputted with an abnormal image; generating, by the recognition model, one or more attribute distributions corresponding to the medical image; generating a marginal likelihood corresponding to the likelihood of a sample image substantially matching the medical image, the sample image generated by sampling, by a generative model, the one or more attribute distributions; comparing the marginal likelihood to a predetermined likelihood threshold; and generating a classification by at least: if the marginal likelihood is greater than or equal to the predetermined likelihood threshold, determining the classification of the medical image to be normal; and if the marginal likelihood is less than the predetermined likelihood threshold, determining the classification of the medical image to be abnormal.

In various embodiments, a system for classifying a medical image includes: an image inputting module configured to input a medical image into a recognition model, the recognition model configured to: generate attribute distributions that are substantially Gaussian when inputted with a normal image, and generate attribute distributions that are substantially non-Gaussian when inputted with an abnormal image; an attribute distribution generating module configured to generate, by the recognition model, one or more attribute distributions corresponding to the medical image; a marginal likelihood generating module configured to generate a marginal likelihood corresponding to the likelihood of a sample image substantially matching the medical image, the sample image generated by sampling, by a generative model, the one or more attribute distributions; a marginal likelihood comparing module configured to compare the marginal likelihood to a predetermined likelihood threshold; and a classification generating module configured to generate a classification by at least: if the marginal likelihood is greater than or equal to the predetermined likelihood threshold, determine the classification of the medical image to be normal, and if the marginal likelihood is less than the predetermined likelihood threshold, determine the classification of the medical image to be abnormal.

In various embodiments, a non-transitory computer-readable medium with instructions stored thereon, that when executed by a processor, causes the processor to perform one or more processes including: inputting a medical image into a recognition model, the recognition model configured to: generate attribute distributions that are substantially Gaussian when inputted with a normal image; and generate attribute distributions that are substantially non-Gaussian when inputted with an abnormal image; generating, by the recognition model, one or more attribute distributions corresponding to the medical image; generating a marginal likelihood corresponding to the likelihood of a sample image substantially matching the medical image, the sample image generated by sampling, by a generative model, the one or more attribute distributions; comparing the marginal likelihood to a predetermined likelihood threshold; and generating a classification by at least: if the marginal likelihood is greater than or equal to the predetermined likelihood threshold, determining the classification of the medical image to be normal; and if the marginal likelihood is less than the predetermined likelihood threshold, determining the classification of the medical image to be abnormal.

Depending upon embodiment, one or more benefits may be achieved. These benefits and various additional objects, features and advantages of the present invention can be fully appreciated with reference to the detailed description and accompanying drawings that follow.

3. BRIEF DESCRIPTION OF THE DRAWINGS

4. DETAILED DESCRIPTION OF THE INVENTION

Certain embodiments of the present invention are directed to object recognition. More particularly, some embodiments of the invention provide methods and systems for classifying an anomaly medical image using variational autoencoder. Merely by way of example, some embodiments of the invention are configured to classify a medical scan image. But it would be recognized that the invention has a much broader range of applicability.

Figure 1:
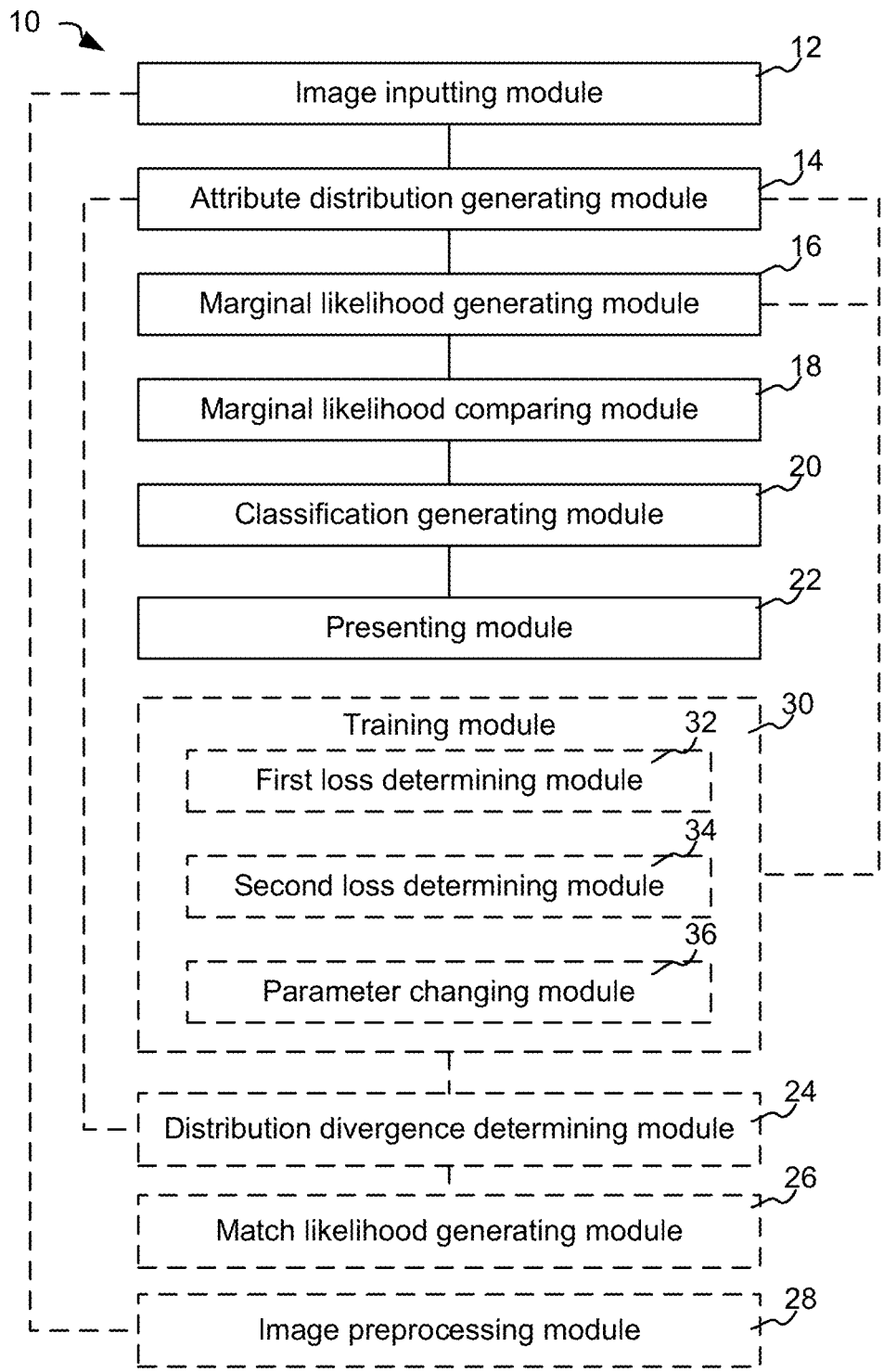
FIG. 1 is a simplified diagram showing a system for classifying a medical image, according to some embodiments.

FIG. 1 is a simplified diagram showing a system for classifying a medical image, according to some embodiments. This diagram is merely an example, which should not unduly limit the scope of the claims. One of ordinary skill in the art would recognize many variations, alternatives, and modifications. In some examples, the system 10 includes an image inputting module 12, an attribute distribution generating module 14, a marginal likelihood generating module 16, a marginal likelihood comparing module 18, a classification generating module 20, and a presenting module 22. In certain embodiments, the system 10 further includes a distribution divergence determining module 24, a match likelihood generating module 26, an image preprocessing module 28, and/or a training module 30. In certain examples, the system 10 is configured to implement method S100 of FIG. 2, the method S200 of FIG. 3, and/or method S300 of FIG. 4. Although the above has been shown using a selected group of components, there can be many alternatives, modifications, and variations. For example, some of the components may be expanded and/or combined. Some components may be removed. Other components may be inserted to those noted above. Depending upon the embodiment, the arrangement of components may be interchanged with others replaced.

In various embodiments, the image inputting module 12 is configured to input a medical image into a recognition model, such as a recognition model of a variational autoencoder. In certain examples, the medical image is two-dimensional. In certain examples, the medical image is three-dimensional. In some examples, the recognition model is an encoder. In some examples, the recognition model is configured to generate one or more attribute distributions that are substantially Gaussian (e.g., more than 50%, 60%, 70%, 80%, or 90% compliant to a Gaussian) when inputted with a normal image (e.g., an image classified as normal), and generate one or more attribute distributions that are substantially non-Gaussian (e.g., less than 40%, 30%, 20%, or 10% compliant to a Gaussian) when inputted with an abnormal image (e.g., an image classified as an anomaly).

In various embodiments, the attribute distribution generating module 14 is configured to generate, by the recognition model, one or more attribute distributions corresponding to the medical image. In some examples, the attribute distribution generating module 14 is configured to generate, by the recognition model, one or more attribute distributions that are substantially Gaussian (e.g., more than 50%, 60%, 70%, 80%, or 90% compliant to a Gaussian) when the medical image is more likely to be a normal image, and generate one or more attribute distributions that are substantially non-Gaussian (e.g., less than 40%, 30%, 20%, or 10% compliant to a Gaussian) when the medical image is more likely to be an abnormal image (e.g., an image classified as an anomaly).

In various embodiments, the marginal likelihood generating module 16 is configured to generate a marginal likelihood corresponding to the likelihood of a sample image substantially matching (e.g., more than 50%, 60%, 70%, 80%, or 90% matching) the medical image. In certain examples, the sample image is generated by sampling, by a generative model, the one or more attribute distributions corresponding to the medical image. In some examples, the generative model is an decoder. In various examples, the generative model is part of a variational autoencoder. In certain examples, the generative model is a multivariate Gaussian model with a diagonal covariance matrix. In some embodiments, the covariance matrix is an identity matrix. In various examples, the marginal likelihood generating module 16 is configured to generate the marginal likelihood using the Monte-Carlo sampling method. In some examples, the Monte-Carlo sampling method utilizes importance sampling. In certain examples, the Monte-Carlo sampling method utilizes Markov chain Monte Carlo.

In various embodiments, the marginal likelihood comparing module 18 is configured to compare the marginal likelihood to a predetermined likelihood threshold. For example, the marginal likelihood comparing module 18 is configured to determine whether the marginal likelihood is greater than or equal to the predetermined likelihood threshold or less than the predetermined likelihood threshold. In certain examples, the predetermined likelihood threshold is predetermined by a medical personnel.

In various embodiments, the classification generating module 20 is configured to generate a classification. In some examples, the classification generating module 20 is configured to, if the marginal likelihood is greater than or equal to the predetermined likelihood threshold, determine the classification of the medical image to be normal. In some examples, the classification generating module 20 is configured to, if the marginal likelihood is less than the predetermined likelihood threshold, determine the classification of the medical image to be abnormal. In some examples, the classification is either normal or abnormal. In certain examples, the classification is either normal or anomaly. In various examples, the classification is represented via an indicator. In some examples, the classification includes a confidence level.

In various embodiments, the presenting module 22 is configured to present the classification and/or the marginal likelihood to a user. For example, the presenting module 22 is configured to present the classification and/or the marginal likelihood as guidance.

In various embodiments, the distribution divergence determining module 24 is configured to determine one or more distribution divergences based at least in part on comparing the one or more attribute distributions to a reference distribution (e.g., a Gaussian distribution or a non-Gaussian distribution) (e.g., a Gaussian distribution or a non-Gaussian distribution). In some examples, the reference distribution (e.g., a Gaussian distribution or a non-Gaussian distribution) is a normal distribution, such as a zero-mean unity-variance distribution. In certain examples, the one or more distribution divergences is one or more Kullback-Leibler divergences.

In various embodiments, the match likelihood generating module 26 is configured to generate a match likelihood based at least in part on the one or more distribution divergences. In some examples, the match likelihood corresponding to the likelihood of the sample image substantially matching (e.g., more than 50%, 60%, 70%, 80%, or 90% matching) the medical image. In certain examples, the higher the match likelihood the more likely the medical image is a normal image rather than an abnormal image. In certain examples, the lower the match likelihood the more likely the medical image is an abnormal image rather than a normal image.

In various embodiments, the image preprocessing module 28 is configured to slice a three-dimensional image into a plurality of two-dimensional images. In some examples, the image preprocessing module 28 is configured to compress an image into a compressed image. In certain examples, the image preprocessing module 28 is configured to extract one or more pertinent features from an image using an autoencoder. In various examples, the image preprocessing module 28 is configured to reduce the dimensionality of an image.

In various embodiments, the training module 30 is configured to train the recognition model and the generative model. In some examples, the training module includes a first loss determining module 32, a second loss determining module 34, and a parameter changing module 36. In various examples, the training module 30 is configured to input (e.g., through the image inputting module 12) a training image into the recognition model. In some examples, the training image is a normal image. In certain examples, the training image is two-dimensional. In certain examples, the training image is three-dimensional. In various examples, the training module 30 is configured to generate (e.g., through the attribute distribution generating module 14), using the recognition model, one or more training attribute distributions corresponding to the training image. In some examples, the training module 30 is configured to determine (e.g., through the first loss determining module 32) a first loss corresponding to the likelihood of a training sample image deviating from the training image. In some examples, the training sample image is generated by sampling, by the generative model, the one or more training attribute distributions. In some examples, the training module 30 is configured to determine (e.g., through the distribution divergence determining module 24) one or more training distribution divergences (e.g., Kullback-Leibler divergences) based at least in part on comparing the one or more training attribute distributions to a reference distribution (e.g., a Gaussian distribution or a non-Gaussian distribution), such as a normal distribution having a mean of zero and a variance of unity. In some examples, the training module 30 is configured to determine (e.g., through the second loss determining module 34) a second loss corresponding to the one or more training distribution divergences. In some examples, the training module 30 is configured to change (e.g., through the parameter changing module 36) one or more parameters of the recognition model and/or one or more parameters of the generative model to reduce, such as minimize the first loss and/or the second loss. For example, the training module 30 is configured to change (e.g., through the parameter changing module 36) one or more parameters of the recognition model and/or one or more parameters of the generative model simultaneously to reduce the sum of the first loss and the second loss. In some examples, the training module 30 is configured to repeatedly train the recognition model and the generative model by inputting one or more additional training images (e.g., into the recognition model). In various examples, the training image and/or the medical image are patient images including one or more shared (e.g., common) patient features. For example, a variational autoencoder configured to help classify images of a particular human joint is trained with training data of the particular human joint.

Figure 2:
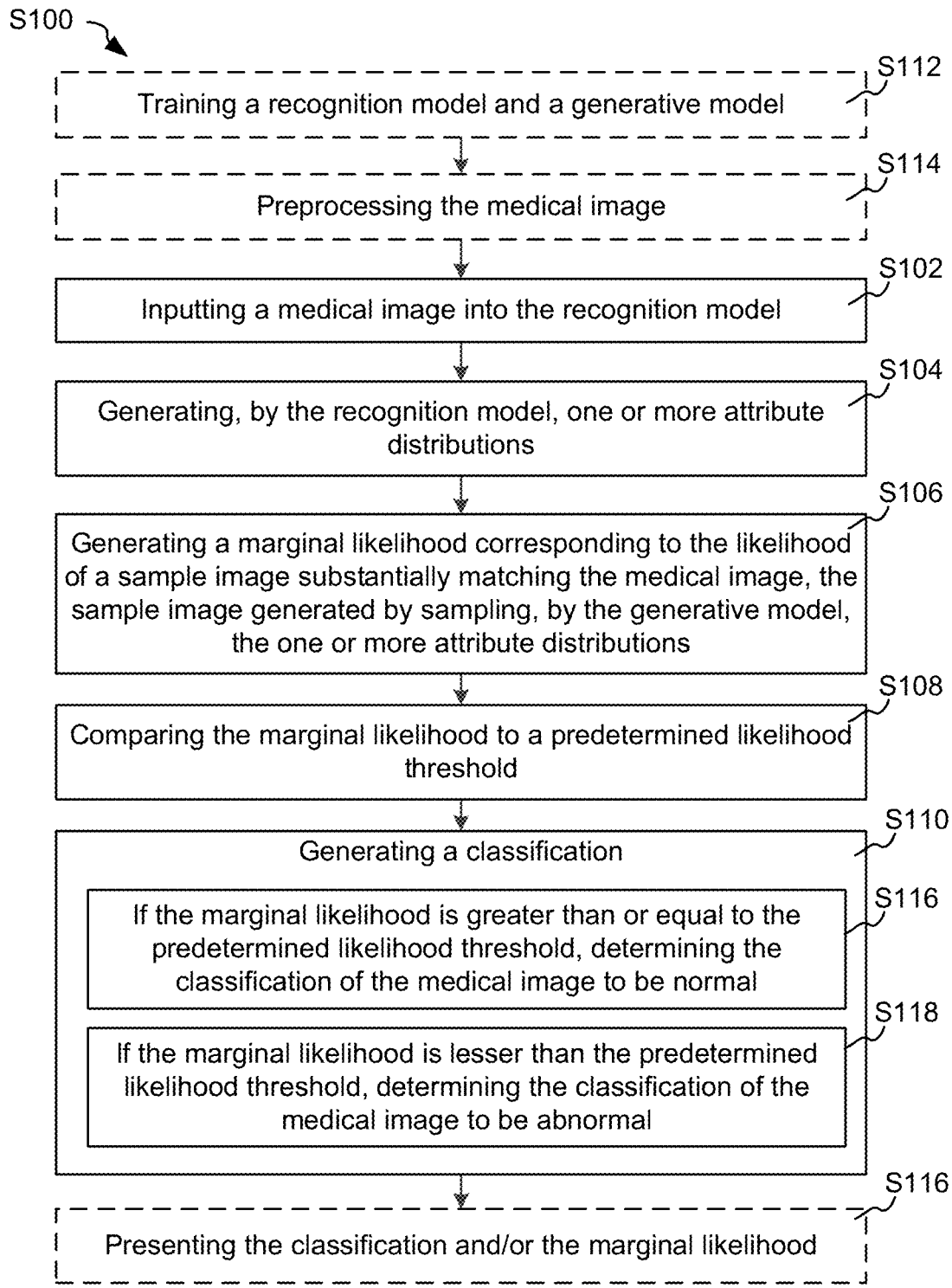
FIG. 2 is a simplified diagram showing a method for classifying a medical image, according to some embodiments.

FIG. 2 is a simplified diagram showing a method for classifying a medical image, according to some embodiments. This diagram is merely an example, which should not unduly limit the scope of the claims. One of ordinary skill in the art would recognize many variations, alternatives, and modifications. In certain examples, the method S100 is implemented by the system 10 of FIG. 1. In some examples, the method S100 includes a process S102 of inputting a medical image into a recognition model, a process S104 of generating one or more attribute distributions, a process S106 of generating a marginal likelihood, a process S108 of comparing the marginal likelihood, a process S110 of generating a classification. In certain examples, the method S100 further includes a process S112 of training a recognition model and a generative model, a process S114 of preprocessing a medical image, and/or a process S116 of presenting the classification and/or the marginal likelihood. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S102 of inputting a medical image into a recognition model. In some examples, the recognition model is configured to generate one or more attribute distributions that are substantially Gaussian (e.g., more than 50%, 60%, 70%, 80%, or 90% compliant to a Gaussian) when inputted with a normal image. In some examples, the recognition model is configured to generate one or more attribute distributions that are substantially non-Gaussian (e.g., less than 40%, 30%, 20%, or 10% compliant to a Gaussian) when inputted with an abnormal image.

In various embodiments, the process S104 of generating one or more attribute distributions includes generating, by the recognition model, one or more attribute distributions corresponding to the medical image. In some examples, generating one or more attribute distributions includes generating, by the recognition model, one or more attribute distributions that are substantially Gaussian (e.g., more than 50%, 60%, 70%, 80%, or 90% compliant to a Gaussian) when the medical image is more likely to be a normal image, and generating one or more attribute distributions that are substantially non-Gaussian (e.g., less than 40%, 30%, 20%, or 10% compliant to a Gaussian) when the medical image is more likely to be an abnormal image (e.g., an image classified as an anomaly).

In various embodiments, the process S106 of generating a marginal likelihood includes generating a marginal likelihood corresponding to the likelihood of a sample image substantially matching (e.g., more than 50%, 60%, 70%, 80%, 90% similar) the medical image. In various examples, the sample image is generated by sampling, by a generative model, the one or more attribute distributions corresponding to the medical image. In some examples, the generative model is an decoder. In various examples, the generative model is part of a variational autoencoder. In certain examples, the generative model is a multivariate Gaussian model with a diagonal covariance matrix. In some embodiments, the covariance matrix is an identity matrix. In various examples, generating the marginal likelihood includes generate the marginal likelihood using the Monte-Carlo sampling method. In some examples, the Monte-Carlo sampling method utilizes importance sampling. In certain examples, the Monte-Carlo sampling method utilizes Markov chain Monte Carlo.

In various embodiments, the process S108 of comparing the marginal likelihood includes comparing the marginal likelihood to a predetermined likelihood threshold. For example, comparing the marginal likelihood to a predetermined likelihood threshold determining whether the marginal likelihood is greater than or equal to the predetermined likelihood threshold or less than the predetermined likelihood threshold. In certain examples, comparing the marginal likelihood to a predetermined likelihood threshold includes determining, via a user instruction, the predetermined likelihood threshold.

In various embodiments, the process S110 of generating a classification includes, if the marginal likelihood is greater than or equal to the predetermined likelihood threshold, determining the classification of the medical image to be normal. In some examples, generating a classification includes, if the marginal likelihood is less than the predetermined likelihood threshold, determining the classification of the medical image to be abnormal (e.g., an anomaly). In some examples, the classification is either normal or abnormal. In certain examples, the classification is either normal or anomaly. In various examples, the classification is represented via an indicator. In some examples, the classification includes a confidence level.

In various embodiments, the process S112 of training a recognition model and a generative model includes inputting a training image into the recognition model. In some examples, the training image is a normal image. In various examples training the recognition model and the generative model includes generating, using the recognition model, one or more training attribute distributions corresponding to the training image. In various examples training the recognition model and the generative model includes determining a first loss corresponding to the likelihood of a training sample image deviating from the training image. In certain examples, the training sample image is generated by sampling, by a generative model, the one or more training attribute distributions. In various examples training the recognition model and the generative model includes determining one or more training distribution divergences (e.g., Kullback-Leibler divergences) based at least in part on comparing the one or more training attribute distributions to a reference distribution (e.g., a Gaussian distribution or a non-Gaussian distribution), such as a normal distribution having a mean of zero and a variance of unity. In various examples training the recognition model and the generative model includes determining a second loss corresponding to the one or more training distribution divergences. In various examples training the recognition model and the generative model includes changing one or more parameters of the recognition model and one or more parameters of the generative model simultaneously to reduce the sum of the first loss and the second loss. In some examples, training the recognition model and the generative model is repeated by inputting one or more additional training images (e.g., into the recognition model). In certain examples, the training image and/or the medical image are patient images including one or more shared (e.g., common) patient features.

In certain examples, training the recognition model and the generative model includes preprocessing the training image. In some examples, preprocessing the training image includes slicing a three-dimensional training image into a plurality of two-dimensional training images. In some examples, preprocessing the training image includes compressing the training image into a compressed training image. In certain examples, preprocessing the training image includes extracting one or more pertinent features from the training image using an autoencoder (e.g., autoencoder of FIG. 8). In various examples, preprocessing the training image includes reducing the dimensionality of the training image.

In various embodiments, the process S114 of preprocessing the medical image includes slicing a three-dimensional medical image into a plurality of two-dimensional medical images. In some examples, preprocessing the medical image includes compressing the medical image into a compressed medical image. In certain examples, preprocessing the medical image includes extracting one or more pertinent features from the medical image using an autoencoder (e.g., autoencoder of FIG. 8). In various examples, preprocessing the medical image includes reducing the dimensionality of the medical image.

In various embodiments, the process S116 of presenting the classification and/or the marginal likelihood includes presenting the classification and/or the marginal likelihood to a user (e.g., as guidance).

In some embodiments, the method S100 further includes determining one or more distribution divergences based at least in part on comparing the one or more attribute distributions to a reference distribution (e.g., a Gaussian distribution or a non-Gaussian distribution). In some examples, the reference distribution (e.g., a Gaussian distribution or a non-Gaussian distribution) is a normal distribution, such as a zero-mean unity-variance distribution. In certain examples, the one or more distribution divergences is one or more Kullback-Leibler divergences. In various examples, the method S100 further includes generating a match likelihood based at least in part on the one or more distribution divergences. In some examples, the match likelihood corresponding to the likelihood of the sample image substantially matching (e.g., more than 50%, 60%, 70%, 80%, or 90% matching) the medical image. In certain examples, the higher the match likelihood the more likely the medical image is a normal image rather than an abnormal image. In certain examples, the lower the match likelihood the more likely the medical image is an abnormal image rather than a normal image.

Figure 3:
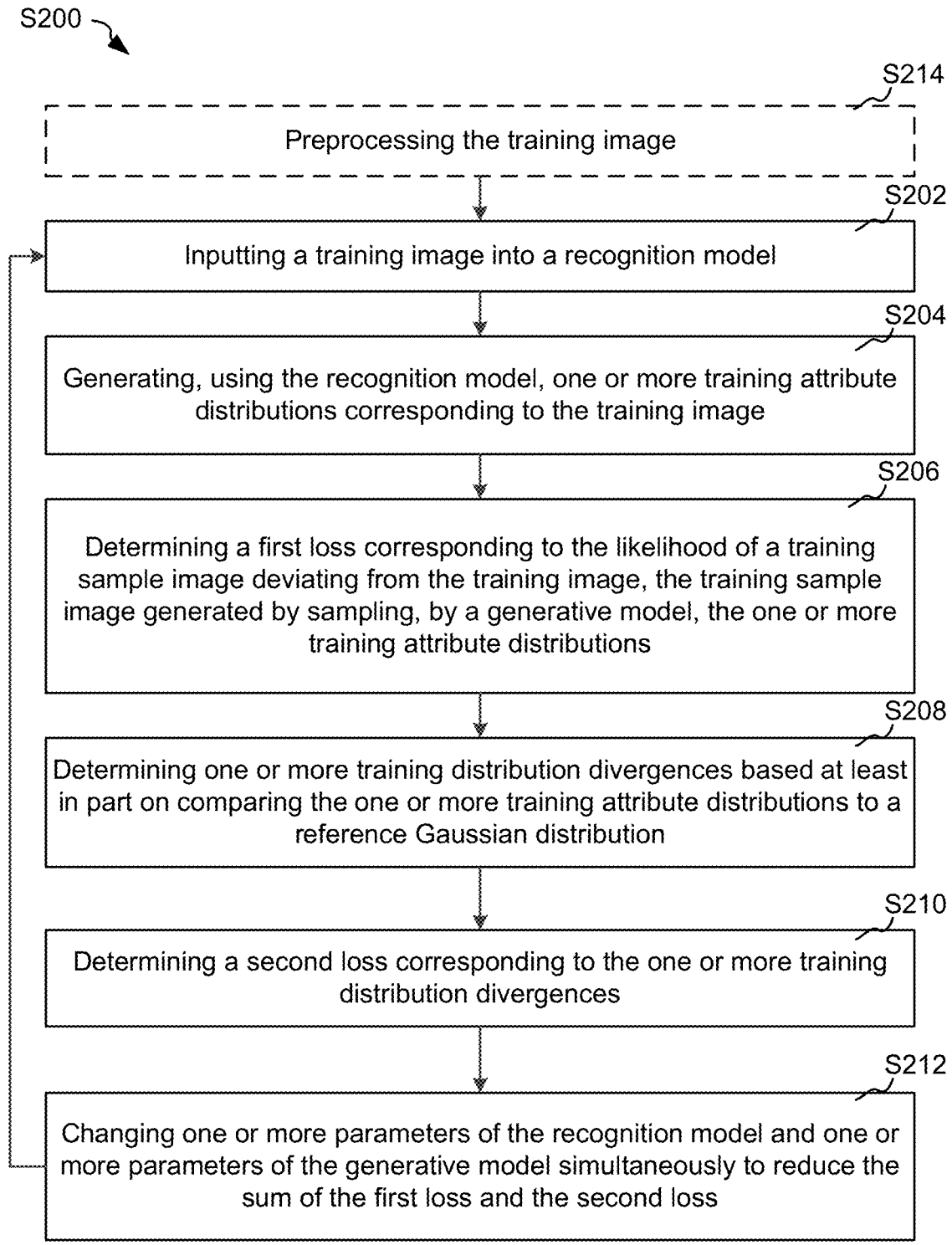
FIG. 3 is a simplified diagram showing a method for training a variational autoencoder for classifying a medical image, according to some embodiments.

FIG. 3 is a simplified diagram showing a method for training a variational autoencoder (e.g., including a recognition model and a generative model) for classifying a medical image, according to some embodiments. This diagram is merely an example, which should not unduly limit the scope of the claims. One of ordinary skill in the art would recognize many variations, alternatives, and modifications. In certain examples, the method S200 is implemented by the system 10 of FIG. 1. In some examples, the method S200 includes a process S202 of inputting a training image into a recognition model, a process S204 of generating one or more training attribute distributions, a process S206 of determining a first loss, a process S208 of determining one or more training distribution divergences, a process S210 of determining a second loss, and a process S212 of changing one or more parameters. In certain examples, the method S200 further includes a process S214 of preprocessing the training image. In some examples, the method S200 is substantially similar to the process S112 of FIG. 2. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

In various embodiments, the process S202 of inputting a training image into a recognition model includes inputting the training image into the recognition model similar to the inputting the medical into the recognition model.

In various embodiments, the process S204 of generating one or more training attribute distributions includes generating one or more training attribute distributions corresponding to the training image, such as similar to the generating one or more attribute distributions corresponding to the medical image.

In various embodiments, the process S206 of determining a first loss includes determining a first loss corresponding to the likelihood of a training sample image deviating from the training image. In some examples, the training sample image is generated by sampling, by a generative model, the one or more training attribute distributions.

In various embodiments, the process S208 of determining one or more training distribution divergences includes determining one or more training distribution divergences (e.g., Kullback-Leibler divergences) based at least in part on comparing the one or more training attribute distributions to a reference distribution (e.g., a Gaussian distribution or a non-Gaussian distribution), such as a normal distribution having a mean of zero and a variance of unity.

In various embodiments, the process S210 of determining a second loss includes determining a second loss corresponding to the one or more training distribution divergences.

In various embodiments, the process S212 of changing one or more parameters includes changing one or more parameters of the recognition model and one or more parameters of the generative model simultaneously to reduce the sum of the first loss and the second loss.

In various embodiments, the process S214 of preprocessing the training image includes slicing a three-dimensional training image into a plurality of two-dimensional training images. In some examples, preprocessing the training image includes compressing the training image into a compressed training image. In certain examples, preprocessing the training image includes extracting one or more pertinent features from the training image using an autoencoder (e.g., autoencoder of FIG. 8). In various examples, preprocessing the training image includes reducing the dimensionality of the training image.

Figure 4:
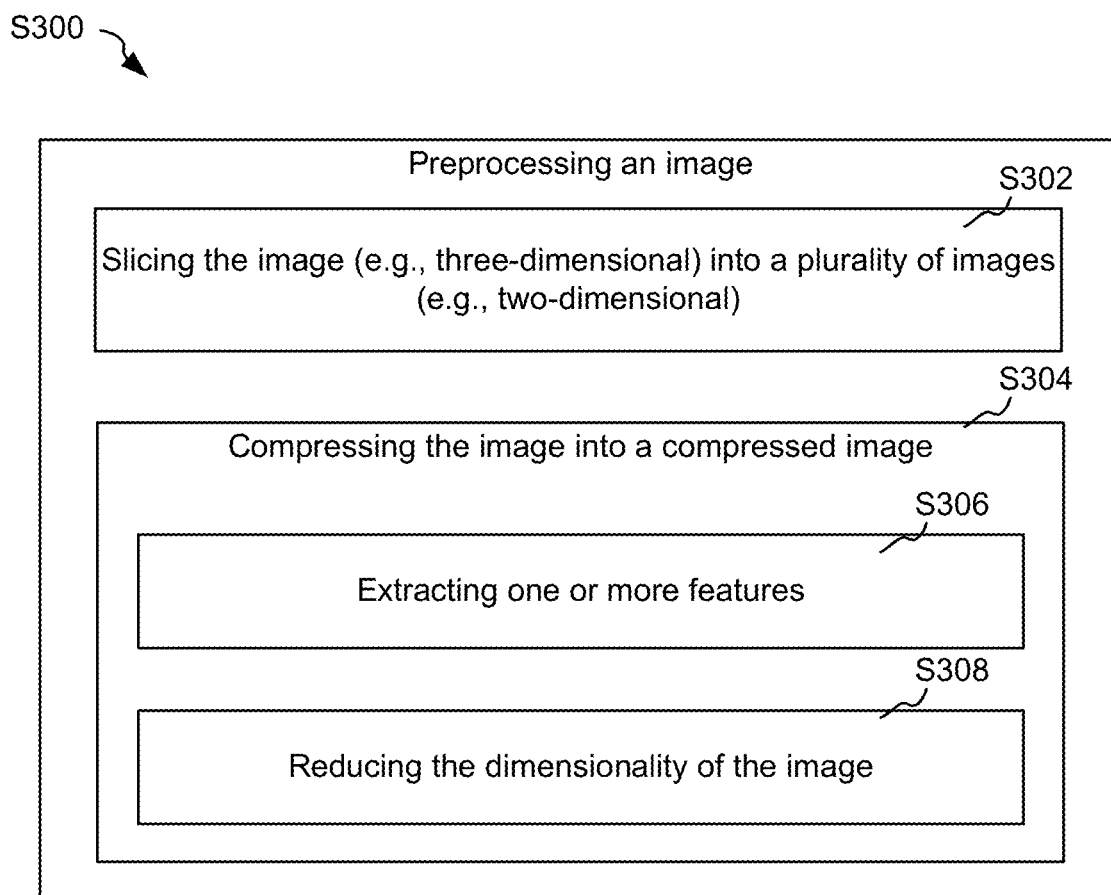
FIG. 4 is a simplified diagram showing a method for preprocessing an image, according to some embodiments.

FIG. 4 is a simplified diagram showing a method for preprocessing an image, according to some embodiments. This diagram is merely an example, which should not unduly limit the scope of the claims. One of ordinary skill in the art would recognize many variations, alternatives, and modifications. In certain examples, the method S300 is implemented by the system 10 of FIG. 1 and is in accordance to the process S114 of FIG. 2 and/or to the process S214 of FIG. 3. In some examples, the method S300 includes a process S302 of slicing the image and/or a process S304 of compressing the image into a compressed image. In certain examples, the process S304 includes a process S306 of extracting one or more features and/or a process S308 of reducing the dimensionality of the image. Although the above has been shown using a selected group of processes for the method, there can be many alternatives, modifications, and variations. For example, some of the processes may be expanded and/or combined. Other processes may be inserted to those noted above. Some processes may be removed. Depending upon the embodiment, the sequence of processes may be interchanged with others replaced.

Figure 5:
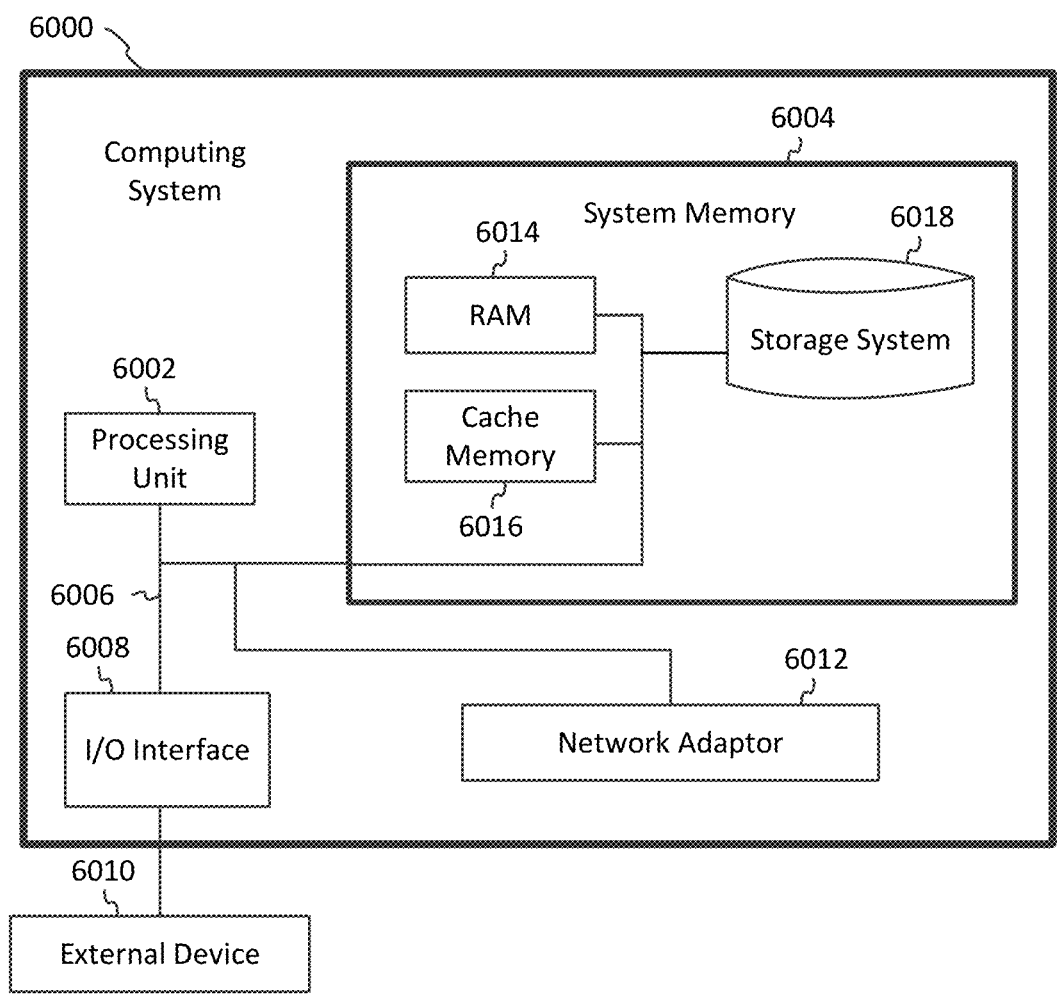
FIG. 5 is a simplified diagram showing a computing system, according to some embodiments.

FIG. 5 is a simplified diagram showing a computing system, according to some embodiments. This diagram is merely an example, which should not unduly limit the scope of the claims. One of ordinary skill in the art would recognize many variations, alternatives, and modifications. In certain examples, the computing system 6000 is a general-purpose computing device. In some examples, the computing system 6000 includes one or more processing units 6002 (e.g., one or more processors), one or more system memories 6004, one or more buses 6006, one or more input/output (I/O) interfaces 6008, and/or one or more network adapters 6012. In certain examples, the one or more buses 6006 connect various system components including, for example, the one or more system memories 6004, the one or more processing units 6002, the one or more input/output (IO) interfaces 6008, and/or the one or more network adapters 6012. Although the above has been shown using a selected group of components for the computing system, there can be many alternatives, modifications, and variations. For example, some of the components may be expanded and/or combined. Other components may be inserted to those noted above. Some components may be removed. Depending upon the embodiment, the arrangement of components may be interchanged with others replaced.

In certain examples, the computing system 6000 is a computer (e.g., a server computer, a client computer), a smartphone, a tablet, or a wearable device. In some examples, some or all processes (e.g., steps) of the method S100, of the method S200, and/or of the method S300 are performed by the computing system 6000. In certain examples, some or all processes (e.g., steps) of the method S100, of the method S200, and/or of the method S300 are performed by the one or more processing units 6002 directed by one or more codes. For example, the one or more codes are stored in the one or more system memories 6004 (e.g., one or more non-transitory computer-readable media), and are readable by the computing system 6000 (e.g., readable by the one or more processing units 6002). In various examples, the one or more system memories 6004 include one or more computer-readable media in the form of volatile memory, such as a random-access memory (RAM) 6014, a cache memory 6016, and/or a storage system 6018 (e.g., a floppy disk, a CD-ROM, and/or a DVD-ROM).

In some examples, the one or more input/output (I/O) interfaces 6008 of the computing system 6000 is configured to be in communication with one or more external devices 6010 (e.g., a keyboard, a pointing device, and/or a display). In certain examples, the one or more network adapters 6012 of the computing system 6000 is configured to communicate with one or more networks (e.g., a local area network (LAN), a wide area network (WAN), and/or a public network (e.g., the Internet)). In various examples, additional hardware and/or software modules are utilized in connection with the computing system 6000, such as one or more micro-codes and/or one or more device drivers.

Figure 6:
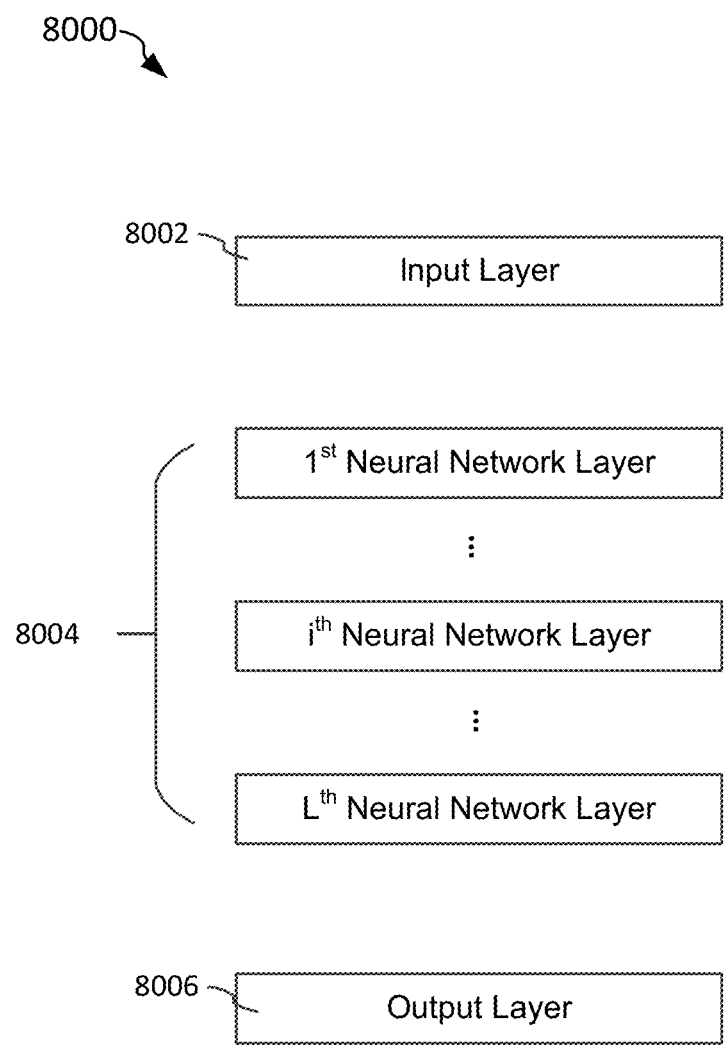
FIG. 6 is a simplified diagram showing a neural network, according to some embodiments.

FIG. 6 is a simplified diagram showing a neural network, according to some embodiments. For example, a neural network is utilized by one or more models, such as the recognition model and/or the generative model. This diagram is merely an example, which should not unduly limit the scope of the claims. One of ordinary skill in the art would recognize many variations, alternatives, and modifications. The neural network 8000 is an artificial neural network. In some examples, the neural network 8000 includes an input layer 8002, one or more hidden layers 8004, and an output layer 8006. For example, the one or more hidden layers 8004 includes L number of neural network layers, which include a $1^{st}$ neural network layer, . . . , an $i^{th}$ neural network layer, . . . and an $L^{th}$ neural network layer, where L is a positive integer and i is an integer that is larger than or equal to 1 and smaller than or equal to L. Although the above has been shown using a selected group of components for the neural network, there can be many alternatives, modifications, and variations. For example, some of the components may be expanded and/or combined. Other components may be inserted to those noted above. Some components may be removed. Depending upon the embodiment, the arrangement of components may be interchanged with others replaced.

In some examples, some or all processes (e.g., steps) of the method S100, of the method S200, and/or of the method S300 are performed by the neural network 8000 (e.g., using the computing system 6000). In certain examples, some or all processes (e.g., steps) of the method S100, of the method S200, and/or of the method S300 are performed by the one or more processing units 6002 directed by one or more codes that implement the neural network 8000. For example, the one or more codes for the neural network 8000 are stored in the one or more system memories 6004 (e.g., one or more non-transitory computer-readable media), and are readable by the computing system 6000 such as by the one or more processing units 6002.

In certain examples, the neural network 8000 is a deep neural network (e.g., a convolutional neural network). In some examples, each neural network layer of the one or more hidden layers 8004 includes multiple sublayers. As an example, the $i^{th}$ neural network layer includes a convolutional layer, an activation layer, and a pooling layer. For example, the convolutional layer is configured to perform feature extraction on an input (e.g., received by the input layer or from a previous neural network layer), the activation layer is configured to apply a nonlinear activation function (e.g., a ReLU function) to the output of the convolutional layer, and the pooling layer is configured to compress (e.g., to down-sample, such as by performing max pooling or average pooling) the output of the activation layer. As an example, the output layer 8006 includes one or more fully connected layers.

As discussed above and further emphasized here, FIG. 6 is merely an example, which should not unduly limit the scope of the claims. One of ordinary skill in the art would recognize many variations, alternatives, and modifications. For example, the neural network 8000 is replaced by an algorithm that is not an artificial neural network. As an example, the neural network 8000 is replaced by a machine learning model that is not an artificial neural network.

In certain embodiments, the systems and methods automatically find anomaly images (non-satisfactory images) generated from medical image scanners, such as automatically using machine learning. In certain examples, systems and methods utilize machine learning to automatically identify candidates of anomaly images. In certain examples, systems and methods utilize variational autoencoder to learn distribution of normal images (e.g., satisfactory images) to help identify candidates of anomaly images, such as with a confidence level or a probability during inference stage, when the images do not correspond to the learned distributions.

In certain embodiments, the variational autoencoder is or includes a generative model, such as a model configured to determine (e.g., estimate) a probability density function of a set of data (e.g., training data). In certain examples, the variational autoencoder is configured to sample examples from the learned probability density function. In some examples, the variational autoencoder is trained to model one or more distributions from training data which corresponding to normal images (e.g., normal medical scan images). In various examples, such as based on sampling distributions determined for a unclassified medical image, the variational autoencoder is configured to assign a high probability value to the image if it is normal, and a low probability value to the image if it is abnormal. In certain embodiments, systems and methods, by utilizing the variational autoencoder, detect medical image anomaly. In certain examples, systems and methods directly find marginal probability of a sample, such as a sample corresponding to one or more distributions, such as without sampling from a latent space, such as without adversary training.

Figure 7:
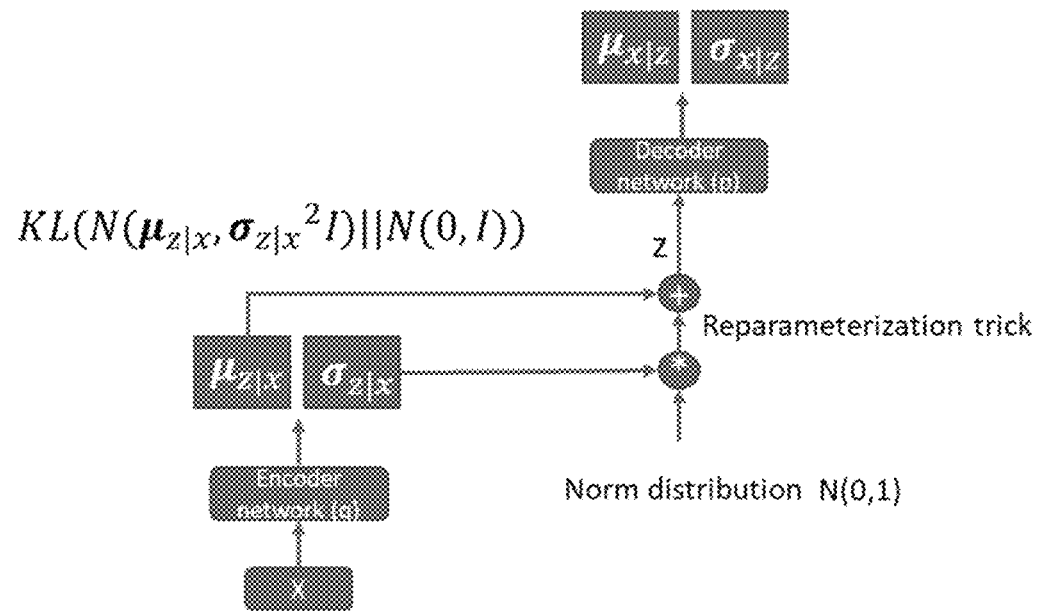
FIG. 7 is a simplified diagram showing a variational autoencoder structure or workflow, according to some embodiments.

FIG. 7 is a simplified diagram showing a variational autoencoder structure or workflow, according to some embodiments. In certain examples, the variational autoencoder of FIG. 7 is configured to be used by the system 10 of FIG. 1, such as via the method S100 of FIG. 2 and/or the method S200 of FIG. 3, to classify anomaly images. In certain examples, the variational autoencoder includes an encoder and a decoder. In some examples, the decoder is configured to sample from a modeled distribution. For example, once trained, a decoder is configured to receive (e.g., be fed with) a sample from a standard Gaussian distribution N (0, I) and generate a sample from an original data distribution. In certain examples, the decoder is a multivariate Gaussian with a diagonal covariance matrix, such as an identity matrix. In accordance with various embodiments, Equation (1) depicts an objective function for training an variational autoencoder:

$$L = -D_{KL}(q_\varphi(z|x) \| p_\theta(z)) + E_{q\varphi(z|x)}[\log p_\theta(x|z)] \qquad (1)$$

The first term on the right side represents the Kullback-Leibler (KL) divergence between approximate posterior distribution $q_\varphi(z|x)$ and gaussian distribution $p_\theta(z)$. $\varphi$ represents encoder parameters and $\theta$ represents decoder parameters.

In certain embodiments, training the variational autoencoder includes optimizing $\varphi$ and $\theta$, such as using a plurality of normal images (e.g., good quality images) that are satisfactory in quality as training data. In certain examples, training the variational autoencoder includes learning distributions corresponding to the plurality of normal images. In various examples, such as after the variational autoencoder is trained and/or during an inference stage, methods and systems utilize the variational autoencoder to determine (e.g., estimate) marginal likelihood of a sample X, which represents one or more features of a medical image to be classified. In some examples, X is the medical image itself. For example, sample X represents just one single image without loss of generality. In certain examples, the generative model of the variational autoencoder is configured to generate a sample from the original distribution.

In various examples, methods and systems determine (e.g., estimate) marginal distribution of sample X, P(X), using the Monte-Carlo sampling method. In some examples, determining (e.g., estimating) marginal distribution of sample X, P(X), using the Monte-Carlo sampling method includes: sampling a sample X, generating, such as based on the encoder, latent distribution $q_\varphi(z|x)$ corresponding to sample X; sampling N z from the latent distribution; feeding z to decoder; generating, using the decoder, likelihood of $p_\theta(x|z)$; determining marginal likelihood of $P_M(X)$ based at least in part on Equation (2); and optionally presenting the marginal likelihood to a user (e.g., a technician or a medical staff). For example, the marginal likelihood is presented by way of an indicator that indicates the image quality of an unclassified medical scan image. In some examples, the indicator includes a classification prediction (e.g., normal or abnormal) and/or a confidence level (e.g., in probability).

$$P_M(X) = \frac{1}{N}\left(\sum_{i=1}^{N} p_\theta(x|z_i)\right) \quad (2)$$

In various embodiments, the marginal likelihood indicates the probability that the sample is sampled from distributions corresponding to a normal image. For example, higher marginal likelihood values indicate high probability that the image is a normal image, whereas smaller marginal likelihood values indicate low probability that the image is a normal image.

In certain embodiments, determining (e.g., estimating, approximating) marginal probability using the Monte-Carlo method includes utilizing importance sampling, such as in accordance to Equation (3):

$$P_M(X) = \left(\frac{1}{N}\sum_{i=1}^{N} \frac{p_\theta(z^i) p_\theta(x|z^i)}{q_\varphi(z^i)}\right) \quad (3)$$

where $q_\varphi$ follows distribution of the output of the encoder, and $p_\theta$ follows a normal distribution. In some examples, $q_\varphi$ is the importance distribution which has similar shape as $p_\theta$ but with scale and shift. In certain examples, sampling a sample includes randomly sampling N values $\{z(n)\}$ from the posterior and then estimate the marginal probability using Equation (3).

In certain embodiments, determining (e.g., estimating, approximating) marginal probability using the Monte-Carlo method includes utilizing the Markov chain Monte Carlo method, such as in accordance to Equation (4):

$$P_M(X) = \left(\frac{1}{N}\sum_{i=1}^{N} \frac{q(z^i)}{p_\theta(z) p_\theta(x|z^i)}\right)^{-1} \quad (4)$$

In some examples, sampling a sample includes sampling N values $\{z(n)\}$ from the posterior using the Markov chain Monte Carlo method; fitting a density estimator q(z) (e.g., estimated from the samples) to these samples $\{z(n)\}$; sampling N new values from the posterior; and estimating the marginal probability in accordance to Equation (4).

In certain embodiments, methods and systems train the variational autoencoder by learning normal image distributions corresponding normal images and, once trained, use the variational autoencoder to classify whether a medical image, such as an image reconstructed from scan data of a medical scanner (e.g., CT, MR, PET scanner), is normal or abnormal (e.g., an anomaly). In certain examples, methods and systems generate (e.g., estimate, compute) a marginal likelihood of the sample, based on variational autoencoder using a Monte-Carlo sampling method. In some examples, the Monte-Carlo sampling method utilizes importance sampling. In some examples, the Monte-Carlo sampling method utilizes the Markov chain Monte Carlo method. In certain examples, methods and systems use the marginal likelihood to indicate whether the medical image is an anomaly. For example, methods and systems present the marginal likelihood to a user (e.g., a technician) to indicate the probability of the medical image being an anomaly. In some examples, such as in addition to or in substitution for using marginal likelihood in providing classification guidance, methods and systems determine a loss, such as in accordance to Equation (1), and uses the value of the loss in providing classification guidance. For example, a larger loss value indicates that the sample is highly probable sampled from distributions corresponding to a normal image, whereas a smaller loss value indicates that the sample is highly probable sampled from distributions corresponding to an anomaly image.

In certain embodiments, methods and systems utilize variational autoencoder to estimate the marginal probability of a sample, which corresponds to a medical image's likelihood to be a normal image (e.g., as compared to an anomaly image). In various examples, methods and systems are suitable for various scanner types, and may utilize or include targeted training for a particular application using a particular scanner type, such as using training data originated from that scanner type. In some examples, training data used in the training stage includes only good quality images, such as images reviewed by medical personnel (e.g., specialist, physicians, technicians) and identified as satisfactory in quality (e.g., satisfying a standard).

Figure 8:
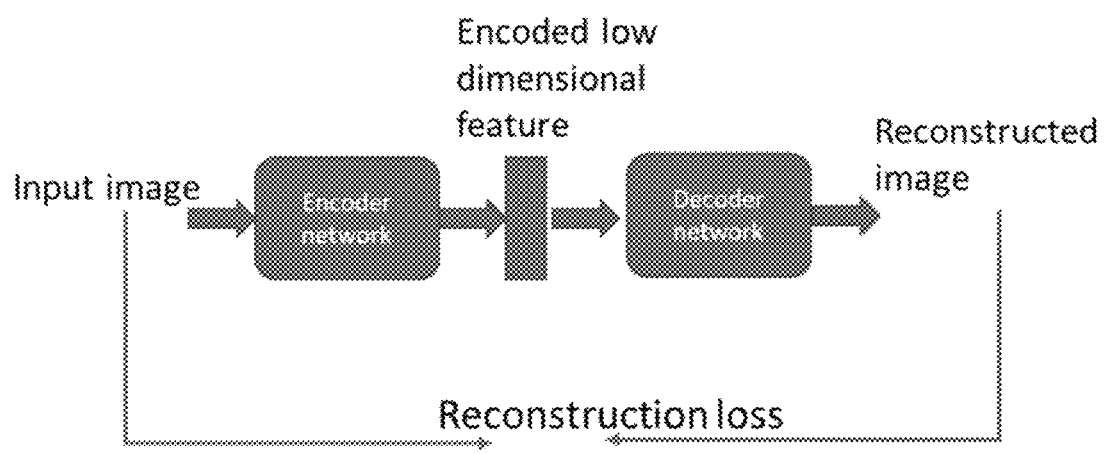
FIG. 8 is a simplified diagram showing an autoencoder structure or workflow, according to some embodiments.

FIG. 8 is a simplified diagram showing an autoencoder structure or workflow, according to some embodiments. In certain examples, the autoencoder of FIG. 8 is configured to be used by the system 10 of FIG. 1, such as via the method S100 of FIG. 2 and/or the method S200 of FIG. 3, to preprocess an input image. In certain embodiments, methods and systems take small-sized images, such as small-sized two-dimensional images, as input. In certain examples, methods and systems take large-sized images, such as large-sized three-dimensional images, as input. In some examples, such as when the input is a three-dimensional image, methods and systems preprocess the input image by slicing the input image into smaller slices, which are then inputted into the variational autoencoder. In certain examples, methods and systems preprocess the input image by compressing the input image to reduce dimensionality and/or extract pertinent features, where the compressed input image is then inputted into the variational autoencoder. In some examples, the compression is performed by the autoencoder depicted. In various examples, an input image (e.g., sample X) is first encoded into low dimensional features (e.g., as output of the encoder). In certain examples, the low dimensional features are then fed into the variational encoder to determine the marginal likelihood for providing classification guidance.

In various embodiments, a computer-implemented method for classifying a medical image includes: inputting a medical image into a recognition model, the recognition model configured to: generate one or more attribute distributions that are substantially Gaussian when inputted with a normal image, and generate one or more attribute distributions that are substantially non-Gaussian when inputted with an abnormal image; generating, by the recognition model, one or more attribute distributions corresponding to the medical image; generating a marginal likelihood corresponding to the likelihood of a sample image substantially matching the medical image, the sample image generated by sampling, by a generative model, the one or more attribute distributions; comparing the marginal likelihood to a predetermined likelihood threshold; and generating a classification by at least: if the marginal likelihood is greater than or equal to the predetermined likelihood threshold, determining the classification of the medical image to be normal; and if the marginal likelihood is less than the predetermined likelihood threshold, determining the classification of the medical image to be abnormal. In certain examples, the computer-implemented method is performed by one or more processors. In some examples, the computer-implemented method is implemented at least partly according to the method S100 of FIG. 2 and/or the method S200 of FIG. 3. In certain examples, the method is implemented at least partly by the system 10 of FIG. 1.

In some embodiments, the method further includes: training the recognition model and the generative model by at least: inputting a training image into the recognition model, the training image being a normal image; generating, using the recognition model, one or more training attribute distributions corresponding to the training image; determining a first loss corresponding to the likelihood of a training sample image deviating from the training image, the training sample image generated by sampling, by a generative model, the one or more training attribute distributions; determining one or more training distribution divergences based at least in part on comparing the one or more training attribute distributions to a reference distribution; determining a second loss corresponding to the one or more training distribution divergences; and changing one or more parameters of the recognition model and one or more parameters of the generative model simultaneously to reduce the sum of the first loss and the second loss.

In some embodiments, the training the recognition model and the generative model is repeated by inputting one or more additional training images (e.g., into the recognition model).

In some embodiments, the training image and/or the medical image are patient images including one or more shared (e.g., common) patient features.

In some embodiments, the one or more training distribution divergences is one or more Kullback-Leibler divergences.

In some embodiments, the reference distribution is a normal distribution having a mean of zero and a variance of unity.

In some embodiments, the method further includes slicing a three-dimensional training image into a plurality of two-dimensional training images.

In some embodiments, the method further includes compressing the training image into a compressed training image.

In some embodiments, the compressing the training image includes extracting one or more pertinent features using an autoencoder.

In some embodiments, the compressing the training image includes reducing the dimensionality of the training image.

In some embodiments, the method further includes slicing a three-dimensional medical image into a plurality of two-dimensional medical images.

In some embodiments, the method further includes compressing the medical image into a compressed medical image.

In some embodiments, the compressing the medical image includes extracting one or more pertinent features using an autoencoder.

In some embodiments, the compressing the medical image includes reducing the dimensionality of the medical image.

In some embodiments, the recognition model is an encoder and the generative model is a decoder. For example, the encoder and the decoder are part of a variational autoencoder.

In some embodiments, the generative model is a multivariate Gaussian model with a diagonal covariance matrix.

In some embodiments, the covariance matrix is an identity matrix.

In some embodiments, the generating a marginal likelihood includes using the Monte-Carlo sampling method.

In some embodiments, the Monte-Carlo sampling method utilizes importance sampling.

In some embodiments, the Monte-Carlo sampling method utilizes Markov chain Monte Carlo.

In some embodiments, the method further includes presenting the classification and/or the marginal likelihood to a user.

In some embodiments, the method further includes: determining one or more distribution divergences based at least in part on comparing the one or more attribute distributions to a reference distribution; and generating a match likelihood based at least in part on the one or more distribution divergences, the match likelihood corresponding to the likelihood of the sample image substantially matching the medical image. In certain examples, the higher the match likelihood the more likely the medical image is a normal image rather than an abnormal image. In certain examples, the lower the match likelihood the more likely the medical image is an abnormal image rather than a normal image.

In some embodiments, the one or more distribution divergences is one or more Kullback-Leibler divergences.

In various embodiments, a system for classifying a medical image includes: an image inputting module configured to input a medical image into a recognition model, the recognition model configured to: generate attribute distributions that are substantially Gaussian when inputted with a normal image, and generate attribute distributions that are substantially non-Gaussian when inputted with an abnormal image; an attribute distribution generating module configured to generate, by the recognition model, one or more attribute distributions corresponding to the medical image; a marginal likelihood generating module configured to generate a marginal likelihood corresponding to the likelihood of a sample image substantially matching the medical image, the sample image generated by sampling, by a generative model, the one or more attribute distributions; a marginal likelihood comparing module configured to compare the marginal likelihood to a predetermined likelihood threshold; and a classification generating module configured to generate a classification by at least: if the marginal likelihood is greater than or equal to the predetermined likelihood threshold, determine the classification of the medical image to be normal, and if the marginal likelihood is less than the predetermined likelihood threshold, determine the classification of the medical image to be abnormal. In some examples, the system is implemented at least partly according to the system 10 of FIG. 1. In certain examples, the system is configured to perform, at least partly, the method S100 of FIG. 2 and/or the method S200 of FIG. 3.

In some embodiments, the system further includes: a training module including a first loss determining module, a second loss determining module, and a parameter changing module. In some examples, the training module is configured to train the recognition model and the generative model by at least: inputting (e.g., through the image inputting module) a training image into the recognition model, the training image being a normal image; generating (e.g., through the attribute distribution generating module), using the recognition model, one or more training attribute distributions corresponding to the training image; determining (e.g., through the first loss determining module) a first loss corresponding to the likelihood of a training sample image deviating from the training image, the training sample image generated by sampling, by a generative model, the one or more training attribute distributions; determining (e.g., through a distribution divergence determining module of the system) one or more training distribution divergences based at least in part on comparing the one or more training attribute distributions to a reference distribution; determining (e.g., through the second loss determining module) a second loss corresponding to the one or more training distribution divergences; and changing (e.g., through the parameter changing module) one or more parameters of the recognition model and one or more parameters of the generative model simultaneously to reduce the sum of the first loss and the secondloss.

In some embodiments, the training module is configured to repeatedly train the recognition model and the generative model by inputting one or more additional training images (e.g., into the recognition model).

In some embodiments, the training image and/or the medical image are patient images including one or more shared (e.g., common) patient features.

In some embodiments, the one or more training distribution divergences is one or more Kullback-Leibler divergences.

In some embodiments, the reference distribution is a normal distribution having a mean of zero and a variance of unity.

In some embodiments, the system further includes an image preprocessing module configured to slice a three-dimensional training image into a plurality of two-dimensional training images.

In some embodiments, the image preprocessing module is configured to compress the training image into a compressed training image.

In some embodiments, the image preprocessing module is configured to extract one or more pertinent features from the training image using an autoencoder.

In some embodiments, the image preprocessing module is configured to reduce the dimensionality of the training image.

In some embodiments, the system further includes an image preprocessing module configured to slice a three-dimensional medical image into a plurality of two-dimensional medical images.

In some embodiments, the image preprocessing module is configured to compress the medical image into a compressed medical image.

In some embodiments, the image preprocessing module is configured to extract one or more pertinent features from the medical image using an autoencoder.

In some embodiments, the image preprocessing module is configured to reduce the dimensionality of the medical image.

In some embodiments, the recognition model is an encoder and the generative model is a decoder. For example, the encoder and the decoder are part of a variational autoencoder.

In some embodiments, the generative model is a multivariate Gaussian model with a diagonal covariance matrix.

In some embodiments, the covariance matrix is an identity matrix.

In some embodiments, the marginal likelihood generating module is configured to generate the marginal likelihood using the Monte-Carlo sampling method.

In some embodiments, the Monte-Carlo sampling method utilizes importance sampling.

In some embodiments, the Monte-Carlo sampling method utilizes Markov chain Monte Carlo.

In some embodiments, the system further includes a presenting module configured to present the classification and/or the marginal likelihood to a user.

In some embodiments, the system further includes a distribution divergence determining module configured to determine one or more distribution divergences based at least in part on comparing the one or more attribute distributions to a reference distribution; and a match likelihood generating module configured to generate a match likelihood based at least in part on the one or more distribution divergences, the match likelihood corresponding to the likelihood of the sample image substantially matching the medical image. In certain examples, the higher the match likelihood the more likely the medical image is a normal image rather than an abnormal image. In certain examples, the lower the match likelihood the more likely the medical image is an abnormal image rather than a normal image.

In some embodiments, the one or more distribution divergences is one or more Kullback-Leibler divergences.

In various embodiments, a non-transitory computer-readable medium with instructions stored thereon, that when executed by a processor, causes the processor to perform one or more processes including: inputting a medical image into a recognition model, the recognition model configured to: generate attribute distributions that are substantially Gaussian when inputted with a normal image; and generate attribute distributions that are substantially non-Gaussian when inputted with an abnormal image; generating, by the recognition model, one or more attribute distributions corresponding to the medical image; generating a marginal likelihood corresponding to the likelihood of a sample image substantially matching the medical image, the sample image generated by sampling, by a generative model, the one or more attribute distributions; comparing the marginal likelihood to a predetermined likelihood threshold; and generating a classification by at least: if the marginal likelihood is greater than or equal to the predetermined likelihood threshold, determining the classification of the medical image to be normal; and if the marginal likelihood is less than the predetermined likelihood threshold, determining the classification of the medical image to be abnormal. In some examples, the non-transitory computer-readable medium with instructions stored thereon is implemented according to the method S100 of FIG. 2 and/or the method S200 of FIG. 3. In certain examples, the non-transitory computer-readable medium with instructions stored thereon is configured to be implemented at least partly by the system 10 (e.g., a terminal) of FIG. 1.

In some embodiments, the non-transitory computer-readable medium with instructions stored thereon, that when executed by a processor, further causes the processor to perform one or more processes including: training the recognition model and the generative model by at least: inputting a training image into the recognition model, the training image being a normal image; generating, using the recognition model, one or more training attribute distributions corresponding to the training image; determining a first loss corresponding to the likelihood of a training sample image deviating from the training image, the training sample image generated by sampling, by a generative model, the one or more training attribute distributions; determining one or more training distribution divergences based at least in part on comparing the one or more training attribute distributions to a reference distribution; determining a second loss corresponding to the one or more training distribution divergences; and changing one or more parameters of the recognition model and one or more parameters of the generative model simultaneously to reduce the sum of the first loss and the second loss.

In some embodiments, the training the recognition model and the generative model is repeated by inputting one or more additional training images (e.g., into the recognition model).

In some embodiments, the training image and/or the medical image are patient images including one or more shared (e.g., common) patient features.

In some embodiments, the one or more training distribution divergences is one or more Kullback-Leibler divergences.

In some embodiments, the reference distribution is a normal distribution having a mean of zero and a variance of unity.

In some embodiments, the non-transitory computer-readable medium with instructions stored thereon, that when executed by a processor, further causes the processor to perform one or more processes including: slicing a three-dimensional training image into a plurality of two-dimensional training images.

In some embodiments, the non-transitory computer-readable medium with instructions stored thereon, that when executed by a processor, further causes the processor to perform one or more processes including: compressing the training image into a compressed training image.

In some embodiments, the compressing the training image includes extracting one or more pertinent features using an autoencoder.

In some embodiments, the compressing the training image includes reducing the dimensionality of the training image.

In some embodiments, the non-transitory computer-readable medium with instructions stored thereon, that when executed by a processor, further causes the processor to perform one or more processes including: slicing a three-dimensional medical image into a plurality of two-dimensional medical images.

In some embodiments, the non-transitory computer-readable medium with instructions stored thereon, that when executed by a processor, further causes the processor to perform one or more processes including: compressing the medical image into a compressed medical image.

In some embodiments, the compressing the medical image includes extracting one or more pertinent features using an autoencoder.

In some embodiments, the compressing the medical image includes reducing the dimensionality of the medical image.

In some embodiments, the recognition model is an encoder and the generative model is a decoder. For example, the encoder and the decoder are part of a variational autoencoder.

In some embodiments, the generative model is a multivariate Gaussian model with a diagonal covariance matrix.

In some embodiments, the covariance matrix is an identity matrix.

In some embodiments, the non-transitory computer-readable medium with instructions stored thereon, that when executed by a processor, causes the processor to perform one or more processes including: generating a marginal likelihood includes using the Monte-Carlo sampling method.

In some embodiments, the Monte-Carlo sampling method utilizes importance sampling.

In some embodiments, the Monte-Carlo sampling method utilizes Markov chain Monte Carlo.

In some embodiments, the non-transitory computer-readable medium with instructions stored thereon, that when executed by a processor, further causes the processor to perform one or more processes including: presenting the classification and/or the marginal likelihood to a user.

In some embodiments, the non-transitory computer-readable medium with instructions stored thereon, that when executed by a processor, further causes the processor to perform one or more processes including: determining one or more distribution divergences based at least in part on comparing the one or more attribute distributions to a reference distribution; and generating a match likelihood based at least in part on the one or more distribution divergences, the match likelihood corresponding to the likelihood of the sample image substantially matching the medical image. In certain examples, the higher the match likelihood the more likely the medical image is a normal image rather than an abnormal image. In certain examples, the lower the match likelihood the more likely the medical image is an abnormal image rather than a normal image.

In some embodiments, the one or more distribution divergences is one or more Kullback-Leibler divergences.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code including program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for classifying, a medical image, the method comprising:
    training a recognition model and a generative model by at least:
        inputting a training image into the recognition model, the training image being a normal image;
        generating, using the recognition model, one or more training attribute distributions corresponding to the training image;
        determining a first loss corresponding to the likelihood of a training sample image deviating from the training image, the training sample image generated by sampling, by the generative model, the one or more training attribute distributions;
        determining one or more training distribution divergences based at least in part on comparing the one or more training attribute distributions to a reference distribution;
        determining a second loss corresponding to the one or more training distribution divergences; and
        changing one or more parameters of the recognition model and one or more parameters of the generative model simultaneously to reduce the sum of the first loss and the second loss;
    inputting a medical image into the recognition model, the recognition model configured to:
        generate one or more attribute distributions that are substantially Gaussian when inputted with a normal image; and
        generate one or more attribute distributions that are substantially non-Gaussian when inputted with an abnormal image;
    generating, by the recognition model, one or more attribute distributions corresponding to the medical image;
    generating a marginal likelihood corresponding to a likelihood of a sample image substantially matching the medical image, the sample image generated by sampling, by the generative model, the one or more attribute distributions;
    comparing the marginal likelihood to a predetermined likelihood threshold; and
    generating a classification by at least:
        if the marginal likelihood is greater than or equal to the predetermined likelihood threshold, determining the classification of the medical image to be normal; and
        if the marginal likelihood is less than the predetermined likelihood threshold, determining the classification of the medical image to be abnormal.

2. The computer-implemented method of claim 1, wherein the training the recognition model and the generative model is repeated by inputting one or more additional training images.

3. The computer-implemented method of claim 1, wherein the training image and the medical image are patient images including one or more shared patient features.

4. The computer-implemented method of claim 1, wherein the one or more training distribution divergences is one or more Kullback-Leibler divergences.

5. The computer-implemented method of claim 1, wherein the reference distribution is a normal distribution having a mean of zero and a variance of unity.

6. The computer-implemented method of claim 1, further comprising slicing a three-dimensional training image into a plurality of two-dimensional training images.

7. The computer-implemented method of claim 1, further comprising compressing the training image into a compressed training image.

8. The computer-implemented method of claim 7, wherein the compressing the training image includes extracting one or more pertinent features using an autoencoder.

9. The computer-implemented method of claim 7, wherein the compressing the training image includes reducing the dimensionality of the training image.

10. The computer-implemented method of claim 1, wherein the recognition model is an encoder and the generative model is a decoder, the encoder and the decoder being part of a variational autoencoder.

11. The computer-implemented method of claim 1, wherein the generative model is a multi variate Gaussian model with a diagonal covariance matrix.

12. The computer-implemented method of claim 11, wherein the covariance matrix is an identity matrix.

13. The computer-implemented method of claim 1, wherein the generating a marginal likelihood includes using the Monte-Carlo sampling method.

14. The computer-implemented method of claim 13, wherein the Monte-Carlo sampling method utilizes importance sampling.

15. The computer-implemented method of claim 13, wherein the Monte-Carlo sampling method utilizes Markov chain Monte Carlo.

16. The computer-implemented method of claim 1, further comprising presenting at least one of the classification and the marginal likelihood to a user.

17. A computer-implemented method for classifying a medical image, the method comprising:
    inputting a medical image into the recognition model the recognition model configured to:
        generate one or more attribute distributions that are substantially Gaussian when inputted with a normal image; and
        generate one or more attribute distributions that are substantially non-Gaussian when inputted with an abnormal image;
    generating, by the recognition model, one or more attribute distributions corresponding to the medical image;
    generating a marginal likelihood corresponding to a likelihood of a sample image substantially matching the medical image, the sample image generated by sampling, by a generative model, the one or more attribute distributions;
    comparing the marginal likelihood to a predetermined likelihood threshold; and
    generating a classification by at least:
        if the marginal likelihood is greater than or equal to the predetermined likelihood threshold, determining the classification of the medical image to be normal;
        if the marginal likelihood is less than the predetermined likelihood threshold, determining the classification of the medical image to be abnormal;
    determining one or more distribution divergences based at least in part on comparing the one or more attribute distributions to a reference distribution; and
    generating a match likelihood based at least in part on the one or more distribution divergences, the match likelihood corresponding to the likelihood of the sample image substantially matching the medical image;
    wherein the higher the match likelihood the more likely the medical image is a normal image rather than an abnormal image;
    wherein the lower the match likelihood the more likely the medical image is an abnormal image rather than a normal image.

18. A non-transitory computer-readable medium with instructions stored thereon, that when executed by a processor, causes the processor to perform the processes including:
    training a recognition model and a generative model by at least:
        inputting a training image into the recognition model, the training image being a normal image;
        generating, using the recognition model, one or more training attribute distributions corresponding to the training image;
        determining a first loss corresponding to the likelihood of a training sample image deviating from the training image, the training sample image generated by sampling, by the generative model, the one or more training attribute distributions;
        determining one or more training distribution divergences based at least in part on comparing the one or more training attribute distributions to a reference distribution;
        determining a second loss corresponding to the one or more training distribution divergences; and
        changing one or more parameters of the recognition model and one or more parameters of the generative model simultaneously to reduce the sum of the first loss and the second loss;
    inputting a medical image into the recognition model, the recognition model configured to:
        generate attribute distributions that are substantially Gaussian when inputted with a normal image; and
        generate attribute distributions that are substantially non-Gaussian when inputted with an abnormal image;
    generating, by the recognition model, one or more attribute distributions corresponding to the medical image;
    generating a marginal likelihood corresponding to a likelihood of a sample image substantially matching the medical image, the sample image generated by sampling, by the generative model, the one or more attribute distributions;
    comparing the marginal likelihood to a predetermined likelihood threshold; and
    generating a classification by at least:
        if the marginal likelihood is greater than or equal to the predetermined likelihood threshold, determining the classification of the medical image to be normal; and
        if the marginal likelihood is less than the predetermined likelihood threshold, determining the classification of the medical image to be abnormal.

* * * * *